United States Patent [19]
Garrison et al.

[11] Patent Number: 5,263,963
[45] Date of Patent: * Nov. 23, 1993

[54] EXPANDABLE CAGE CATHETER FOR REPAIRING A DAMAGED BLOOD VESSEL

[75] Inventors: Michi E. Garrison, Santa Cruz; Timothy R. Machold, Moss Beach, both of Calif.

[73] Assignee: Advanced Cardiovascular Systems, Inc., Calif.

[*] Notice: The portion of the term of this patent subsequent to Jan. 19, 2010 has been disclaimed.

[21] Appl. No.: 682,190

[22] Filed: Apr. 8, 1991

Related U.S. Application Data

[63] Continuation of Ser. No. 404,815, Sep. 8, 1989, Pat. No. 5,043,001.

[51] Int. Cl.$^5$ ............................................. A61M 29/00
[52] U.S. Cl. ...................................... 606/198; 604/104
[58] Field of Search .................. 604/95, 96, 102–104, 604/109, 160; 606/159, 191, 194, 198, 200; 128/656–658

[56] References Cited

U.S. PATENT DOCUMENTS

| | | | |
|---|---|---|---|
| 4,723,549 | 2/1988 | Wholey et al. | 604/101 |
| 4,748,982 | 6/1988 | Horzewski et al. | 604/102 |
| 4,885,003 | 12/1989 | Hillstead | 604/22 |
| 4,921,484 | 5/1990 | Hillstead | 604/104 |
| 4,954,126 | 9/1990 | Wallsten | 606/191 |
| 4,994,032 | 2/1991 | Sugiyama et al. | 604/96 |
| 4,998,539 | 3/1991 | Delsanti | 606/198 |

*Primary Examiner*—John D. Yasko
*Assistant Examiner*—Anthony Gutowski
*Attorney, Agent, or Firm*—Fulwider, Patton, Lee & Utecht

[57] ABSTRACT

A vascular catheter having an expandable cage mounted on the distal end of a tubular member which is radially expanded and contracted by means of a control wire which is secured to the distal end of the expandable cage. The control wire extends through a first inner lumen within the tubular member which extends along essentially the entire length thereof. A second inner lumen is provided in the distal portion of the tubular member which has a proximal port at least 15 but not more than 60 cm from the distal end of the catheter and a distal port which opens into the interior of the expandable cage. A guidewire or a low-profile steerable catheter is slidably disposed within the second lumen and a tubular member such as a slightly expanded coil through the expandable cage interior to facilitate the rapid exchange of the catheter. The catheter assembly is particularly adapted to hold open a blood vessel after a vascular procedure therein such as an angioplasty.

3 Claims, 2 Drawing Sheets

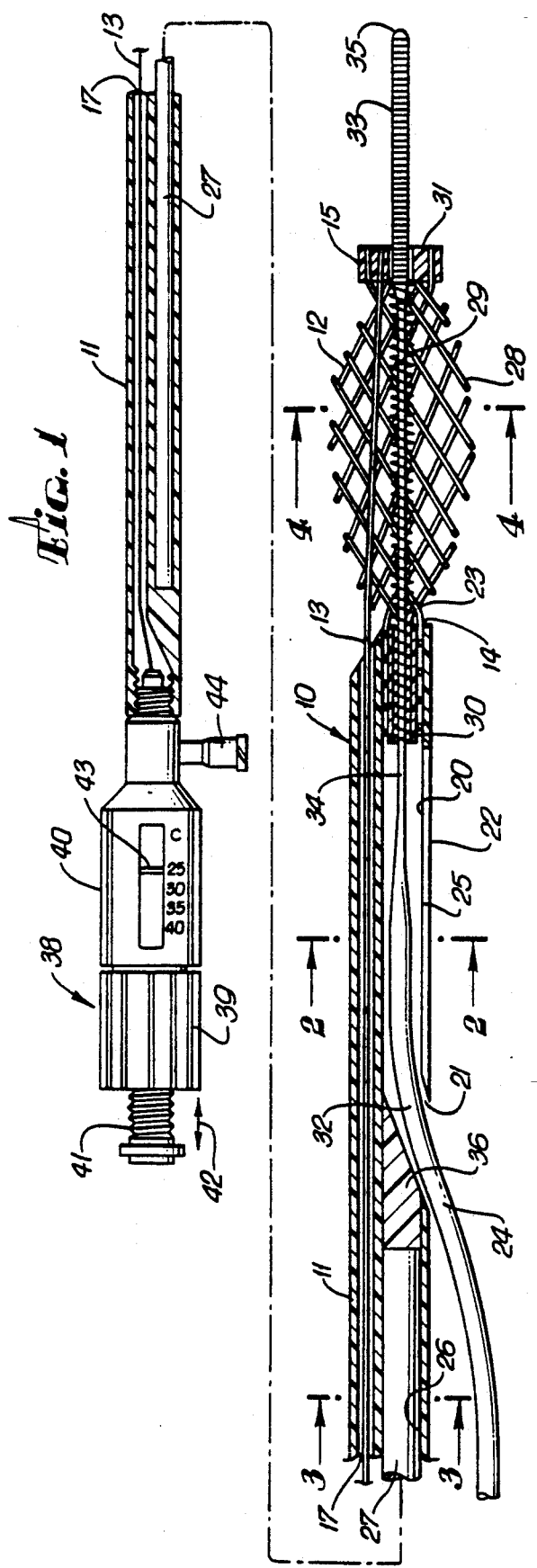

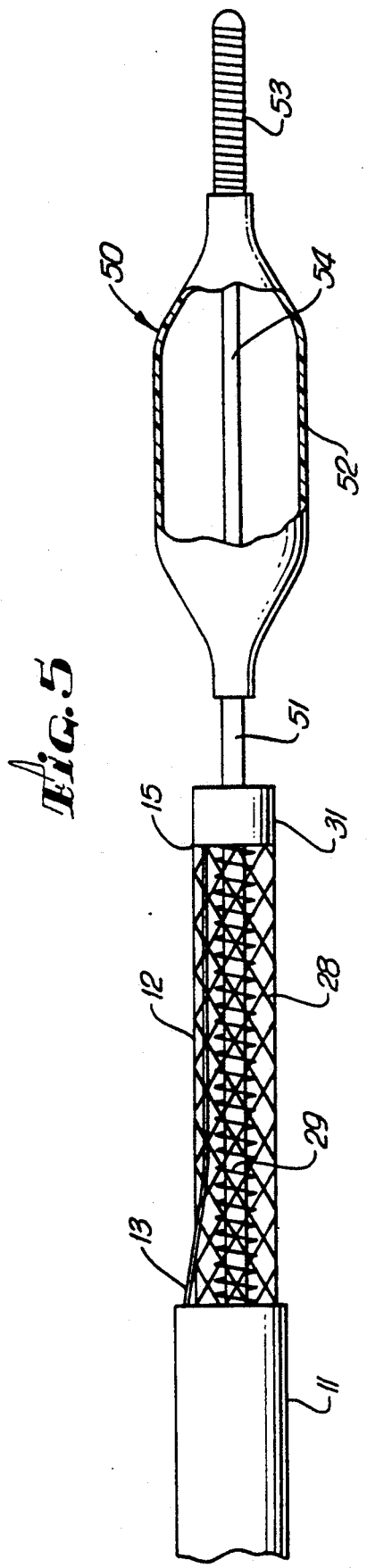

EXPANDABLE CAGE CATHETER FOR REPAIRING A DAMAGED BLOOD VESSEL

This is a continuation of the application Ser. No. 07/404,815 which was filed on Sep. 8, 1989, now U.S. Pat. No. 5,043,001.

BACKGROUND OF THE INVENTION

This invention generally relates to vascular catheters suitable for maintaining the patency of a blood vessel after a vascular procedure therein, such as angioplasty.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced out of the distal end of the guiding catheter into the patient's coronary vasculature until the distal end of the guidewire crosses the lesion to be dilated and then the dilatation catheter is advanced over the previously positioned guidewire until the dilatation balloon is properly located across the lesion. Once in position across the lesion, the flexible, relatively inelastic balloon of the dilatation catheter is inflated to a predetermined size (preferably the same as the inner diameter of the artery at that location) with radiopaque liquid at relatively high pressures (e.g., greater than about 4 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U. S. Pat. No. 4,323,071 (Simpson-Robert); U.S. Pat. No. 4,332,254 (Lindquist); U.S. Pat. No. 4,439,185 (Lundquist); U.S. Pat. No. 4,168,224 (Enzmann et al.); U.S. Pat. No. 4,516,972 (Samson); U.S. Pat. No. 4,582,181 (Samson); U.S. Pat. No. 4,538,622 (Samson et al.); U.S. Pat. No. 4,597,755 (Samson); U.S. Pat. No. 4,616,652 (Simpson); U.S. Pat. No. 4,748,982 (Horzewski et al.); U.S. Pat. No. 4,771,778 (Mar); and U.S. Pat. No. 4,793,350 (Mar et al.) which are hereby incorporated herein in their entirety.

Frequently, the stenotic plaque or intima of the blood vessel or both are dissected during the angioplasty procedure by the inflation of the balloon, so that upon the deflation of the balloon a section of the dissected lining, commonly termed a "flap," will collapse into the bloodstream, closing off blood flow through the vessel and thereby abruptly stopping or significantly reducing the passage of blood therethrough. In these instances, emergency bypass surgery is usually required to avoid a myocardial infarct distal to the blockage.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

Copending application Ser. No. 283,729 filed Dec. 13, 1988, describes an intravascular catheter having an expandable cage on the distal end thereof which is designed to hold a detached lining against an arterial wall for extended periods to facilitate the reattachment thereof. However, this vascular device does not have means to readily advance and withdraw the device over a guidewire.

What has been needed and heretofore unavailable is an easily advanceable and removable low-profile intravascular device which can hold a collapsed dissected lining or flap against the blood vessel wall for sufficient length of time to allow the natural adhesion of the flap to the blood vessel wall while simultaneously allowing for the perfusion of blood distal to the catheter without blocking a branch artery. The present invention satisfies this need.

SUMMARY OF THE INVENTION

This invention is directed to an improved vascular catheter which can hold a blood vessel open for a long period of time after a vascular procedure therein and which also allows for the perfusion of blood through the blood vessel while the blood vessel is held open.

The vascular catheter in accordance with the present invention includes an elongated catheter body formed by a tubular member having a first inner lumen which extends through essentially the entire length of the body and a second, much shorter lumen in the distal portion of the catheter body which is adapted to receive a guiding member therein and which extends through the distal portion from a proximal opening in the sidewall of the distal portion to an opening in the distal end of the catheter body.

An expandable cage formed by a plurality of spirally arranged strands is secured by the proximal end thereof to the distal end of the catheter body. The distal end of the cage is provided with an opening which allows for the passage of a guiding member therethrough.

A control wire extends through the first inner lumen of the tubular member and the interior of the expandable cage with the distal end thereof connected to distal end of the expandable cage. A flexible tubular guide, such as a coiled spring, is provided on the interior of the expandable cage between the ends thereof to ensure the proper passage of the guiding member therethrough. If not properly guided the guiding member can diverge out of the expanded cage through the side thereof. Longitudinal movement of the control wire adjusts the axial spacing between the proximal and distal ends of the expandable cage and thereby changes the radial dimension thereof. Preferably, the control wire is sufficiently stiff so that movement thereof in the distal direction will cause the expandable cage to elongate without bending or kinking the wire. This eliminates the need for biasing the expandable cage in some manner to return to an elongate state with minimal radial dimensions after the expansion thereof to allow for the ready removal of the catheter from the blood vessel. A suitable manipulator is provided on the proximal end of the catheter assembly to longitudinally move the control wire within the first lumen of the tubular member.

The relatively short, second inner lumen disposed within distal portion of the tubular member is preferably defined in part by a sidewall in the distal portion of the tubular member which is provided with an elongated slot extending distally from the proximal hole in the sidewall to a location proximally adjacent the proximal end of the expandable cage. This slotted construction greatly facilitates the rapid exchange of the vascular device of the invention over an in-place guidewire.

The proximal opening or port of the second inner lumen should be spaced proximally more than about 15 cm but less than about 60 cm, preferably from about 20 to about 50 cm, from the distal end of the catheter to ensure that the proximal opening in the sidewall of the tubular body does not extend beyond the distal end of the guiding catheter during a vascular procedure because if the guiding member used is a guidewire, the guidewire tends to form a loop if not restrained in some manner when the vascular catheter of the invention is pulled proximally. Loop formation can interfere with the subsequent removal of the catheter device through the guiding catheter.

In a presently preferred embodiment, the proximal portion of the tubular body is provided with a third inner lumen which has disposed therein a stiffening member or stylet which adds to the pushability of the catheter and facilitates the advancement thereof through a patient's vascular system.

The vascular catheter of the invention allows for the rapid advancement thereof over a guidewire or other guiding member to a vascular location wherein an occlusion has occurred. The cage when expanded will hold the blood vessel open and simultaneously allow blood flow through the expanded cage thereby eliminating or preventing ischemic conditions distal to the occlusion. Importantly, the vascular catheter of the invention can be mounted and withdrawn from an in-place guiding member such as a guidewire without the use of extension wires and the like which can greatly increase the overall time for the procedure. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section, of an intravascular catheter embodying features of the invention;

FIG. 2 is a transverse cross-sectional view of the catheter shown in FIG. 1, taken along the lines 2—2;

FIG. 3 is a transverse cross-sectional view of the catheter shown in FIG. 1 taken along the line 3—3;

FIG. 4 is a transverse cross-sectional view of the catheter shown in FIG. 1 taken along the lines 4—4; and FIG. 5 is an elevational view of the intravascular device shown in FIG. 1, wherein the guiding member is a steerable low-profile dilatation catheter.

DETAILED DESCRIPTION OF THE INVENTION

FIGS. 1-4 illustrate an intravascular catheter assembly 10 embodying features of the invention. The assembly 10 generally includes an elongated catheter body 11, an expandable cage 12 secured within the distal end of the catheter body and a control wire or cable 13 for adjustment of the axial distance between the proximal end 14 and distal end 15 of the expandable cage 12 to vary the radial expansion thereof.

The elongated tubular member which forms the catheter body 11 has a first inner lumen 17 which extends through essentially the entire length thereof and which is adapted to receive control wire 13 and a second much shorter inner lumen 20 in the distal portion of the catheter body 11 which extends from side port 21 in the sidewall 22 of the tubular catheter body 11 to port 23 provided in the distal end of the catheter body. A guiding member 24 is slidably disposed within the relatively short inner lumen 20 to facilitate the rapid advancement and replacement of the catheter assembly 10. A longitudinal slit 25 is preferably provided in the sidewall 22 which extends distally from the side port 21. A third inner lumen 26 may be provided within the catheter body 11 which extends from a location proximal to the side port 21 to essentially the proximal end of the tubular member. A rod or stylet 27 fits within the third inner lumen 26 to provide additional stiffness to the catheter assembly 10 proximal to the side port 21 to increase its pushability.

The expandable cage 12 is formed from a plurality of spirally arranged wires 28, preferably of stainless steel or a radiopaque alloy such as platinum-nickel alloy, which have diameters from about 0.001 to about 0.005 inch, preferably from about 0.002 to about 0.004 inch. The number of wires 28 forming the cage 12 typically varies from about 4 to 20 wires. Wires made from radiopaque materials such as platinum-nickel alloys should be greater than 0.0025 inch in diameter in order to be observed within a patient by fluoroscopic examination. A slightly stretched (e.g., 25%) helical coil 29 is provided within the interior of the cage 12 between the proximal and distal ends 14 and 15 thereof to guide guiding member 24 through the interior the cage. The proximal ends of the wires 28 are bonded between an inner sleeve 30 and the inner surface of the second inner lumen 20. The distal ends of the wires 28 are bonded together by suitable means such as brazing, soldering or welding to form a collar 31. The distal end of control wire 13 is also fixed to distal collar 31 so that longitudinal or axial movement thereof adjusts the axial spacing between the proximal and distal ends 14 and 15 of the cage thereby varying the radial dimension thereof. The wires 28 of the cage 12 should have sufficient strength and be used in sufficient numbers so that the cage is capable of supporting an external pressure of at least about 4 psi to ensure that a flap can be properly held in position within patient's artery.

The guiding member 24, here a guidewire comprises a core member 32, a helical coil 33 or other flexible body disposed about and fixed to the tapered distal portion 34 of the core member. A rounded plug 35, preferably formed of radiopaque material, is provided at the distal tip of the coil 33. The construction of the distal portion of the guidewire 24 can have a conventional structure with the core member 32 extending through helical coil 33 to the plug 35 or with the core member terminating short of the plug 35 and a shaping ribbon (not shown) extending from the core member 32 to the plug 35. The guiding member 24 extends through the second inner lumen 20 disposed within the distal portion of the elongated tubular member which forms the catheter body 11 and out the distal port 23, through the coiled guiding spring 29 which extends through the interior of the expandable cage 12 and out the distal end thereof through the distal collar 31. An incline or ramp 36 is provided at the proximal end of the second inner lumen 20 at the entryway of side port 21 to facilitate the insertion and withdrawal of the guiding member 24 therethrough.

The distance between the distal end 15 of the expandable cage 12 and the side port 21 should be at least 15 cm but not greater than 60 cm, preferably from about 20 to about 50 cm, so that when the cage is expanded within a patient's vascular system to hold a blood vessel open, the side port 21 of the catheter assembly 10 will remain within the interior of a guiding catheter to ensure that the guiding member 24 does not have the opportunity to form a loop when the catheter assembly 10 is pulled back into the guiding catheter.

A manipulator adapter 38 is provided on the proximal end of the catheter body 11 to effect longitudinal movement of the control wire 13. Internally threaded cap 39 is secured to the proximal end of the manipulator housing 40. Axial rotation of the cap 39 causes the longitudinal movement of the internal member 41, as shown by arrow 42, and as a result controls the axial spacing between the ends 14 and 15 of the cage 12 and thus the radial dimension thereof. If the control wire 13 is relatively stiff, it can be employed to extend the ends 14 and 15 of the cage 12 away from one another, elongating the cage so that it can be removed from a blockage. If not, the wire 13 can be used to shorten the spacing between the ends 14 and 15, but the wires 28 of the cage can be formed in a biased condition so that upon release of the handle 38, the cage 12 returns to its elongated condition. An indicator 43 is provided on the internal member 41 to display the radial dimension of the cage 12.

Other means can be employed to return the expanded cage 12 to an elongated condition. For example, as previously mentioned, the ends 14 and 15 may be biased to cause the same elongation, by such means as a spring connected between ends 14 and 15. Additionally, the cage can be formed of nitinol which has a "memory" to allow the cage 12 to change shape with changes in temperature. An electrical current can be passed through the wires to resistively heat the wires and thereby change the shape thereof.

The manipulator 38 has a side arm 44 to inject heparinized saline or other solutions through the first inner lumen 17 to keep the lumen free of blood and to prevent the formation of thrombi in the inner lumen or in the expandable cage 12. Further details of the manipulator 38 can be found in copending application Ser. No. 775,143 filed Oct. 11, 1997 by the present inventors, entitled A RAPIDLY EXCHANGEABLE AND EXPANDABLE CAGE CATHETER FOR REPAIRING DAMAGED BLOOD VESSELS.

Generally, the dimensions of the catheter assembly of the invention are essentially the same dimensions of vascular catheters used in angioplasty procedures. The overall length of the assembly may be about 100 to about 175 cm. The diameter of the catheter body may range from about 0.035 to 0.06 inch. The expandable cage in the unexpanded condition has approximately the same diameter as the catheter body but may be expanded to a maximum diameter of about 1 to about 10 mm. The diameter of the first inner lumen 17 will depend upon the size of the control wire 13 and the amount of fluid which will be passed therethrough. The diameter of the second inner lumen 17 should be sufficiently larger than the diameter of the guiding member 24 to allow the catheter to be easily advanced and removed over the guiding member.

In the operation of the catheter assembly 10, the distal end thereof is mounted onto the proximal end of a guiding member 24 such as a guidewire which has been positioned within the patient's vasculature with the distal portion of the guiding member positioned across the occluded portion of the arterial passageway. The proximal end of the guiding member is advanced proximally through the central passageway provided in the distal collar 31, guided through the interior of the expandable cage 12 by the helical coil 29 through the port 23 leading into the second inner lumen, through the second lumen, and then out the side port 21. The proximal portion of the guiding member 24 extending out of the side port 21 is then manually held while the catheter assembly 10 is advanced over the guiding member through a previously positioned guiding catheter to a desired location within the patient's blood vessel, such as where a prior vascular procedure has been performed. The cap 39 on the manipulator 38 is rotated to expand the cage 12 and thereby to press a flap which may be obstructing the blood flow against the arterial wall and thereby maintain the patency of the artery. The cage 12 is held in the expanded condition for sufficient time, typically about 15 minutes to 24 hours, to allow the dissected lining to heal with the flap being reattached to the artery wall. Treatment periods of up to three days or more are believed to be beneficial. During the period of cage expansion, blood flows readily through the open weave structure of the cage so that no ischemia occurs distal to the catheter either in the occluded artery or a side branch thereof.

After the detached flap has been resecured to the artery wall, the expanded cage 12 can be elongated by rotating the cap in a direction opposite to the direction for expanding the cage to reduce the radial dimensions thereof. Then the catheter assembly 10 can be removed from the location within the patient's vasculature.

As the distal section of the catheter body emerges from the proximal end of the guiding catheter, the guiding member 24 can be separated from the second inner lumen by pulling the guidewire through the slit 25 which extends from the side port 21 to a location adjacent the proximal end of the wires 28 of the cage 12. This allows the guiding member to be manually held exterior to the guiding catheter while the catheter assembly 10 of the invention is being exchanged for another catheter device.

FIG. 5 illustrates an embodiment of the invention wherein the guiding member 24 is a steerable low-profile dilatation catheter 50 which includes a tubular member 51, a dilatation balloon 52 and a helical coil 53 which is disposed about and secured to a core member 54. The proximal end of core member 54 may be secured to the interior of the distal portion of tubular member 51 or it may extend to the proximal end thereof. Further details of steerable dilatation catheters which are suitable for use as guiding members herein can be found in U.S. Pat. No. 4,582,181 (Samson); U.S. Pat. No. 4,771,778 (Mar) and U.S. Pat. No. 4,793,350 (Mar et al.), which have been previously incorporated herein, and copending application Ser. No. 289,919 filed Dec. 23, 1988, entitled STEERABLE DILATATION CATHETER which is hereby incorporated herein in its entirety by reference. The operation and construction of these steerable dilatation catheters are adequately described in the aforesaid references and need not be repeated herein.

The catheter assembly of the invention is described herein to be employed after an angioplasty procedure to hold open an artery when a dissected portion of the arterial lining collapses and occludes the arterial lumen. The assembly shown in FIG. 1 is particularly suitable for use with angioplasty catheters (not shown) having removable guiding members 24 such as disclosed in U.S. Pat. No. 4,323,071 previously referred to. The embodiment shown in FIG. 5 on the other hand includes a guiding member which is a low-profile steerable dilatation catheter. It will be recognized by those skilled in the art that the catheter of the invention can be used within a patient's vascular system after vascular procedures other than angioplasty.

The catheter assembly of the invention may be formed of conventional materials of construction. For example, the catheter body 11 can be made of suitable plastic material such as polyethylene, polyvinylchloride, polyesters and the like. The proximal portion is preferably formed of a suitable metal such as stainless steel (i.e., hypotubing) to provide additional pushability to the catheter assembly. The control wire 13 and the wires 28 forming the cage 12 may be formed of stainless steel but may be formed of other materials such as platinum-nickel alloys (e.g., 90 wt % Pt.—10 wt % NI) or suitable plastics or even composites.

As can be appreciated, various modifications can be made to the present invention. For example, the catheter assembly of the invention may be provided with an inflatable dilatation balloon proximal or distal to the expandable cage. In this manner after dilatation of a stenosis by such a balloon, the position of the catheter assembly can be quickly shifted to position the expandable cage thereof within the occlusion so it can be expanded to hold open the arterial passageway for sufficient time to tack up the flap against the arterial wall. Other modifications can be made to the present invention without departing from the scope thereof.

What is claimed is:

1. A vascular catheter for repairing a section of a lining, comprising:
    a. an elongated catheter body having a relatively long proximal portion with a stiffening means, a relatively short distal portion, a first lumen which extends longitudinally within the catheter body over essentially the entire length thereof and a second, much shorter, lumen which is adapted to receive a guiding member therein and which extends longitudinally within the distal portion of the catheter body between a proximal side opening therein and an opening in the distal end thereof and which is defined at least in part by a sidewall of the distal section having a slit therein which extends distally from the side opening and which facilitates the rapid removal of the catheter from a guiding member within the second lumen;
    b. an expandable cage secured to the distal end of the catheter body which is formed of a plurality of strands, which has a distal end and a proximal end with openings therein and which has sufficient radial strength in the expanded condition to hold open a damaged section of an arterial lining;
    c. an elongated control wire disposed within the first lumen with the distal end thereof secured to the distal end of the expandable cage and;
    d. means on the proximal end of the control wire to move the control wire proximally within the first lumen to decrease the axial distance between the proximal and distal ends of the expandable cage and thereby radially expand the expandable cage to hold open a damaged section of an arterial lining and to move the control wire distally within the first lumen to increase the axial distance between the ends of the expandable cage and thereby radially contract the expandable cage sufficiently to remove the expandable cage from the damaged section of the arterial lining;
    e. wherein the expandable cage is formed from about 4 to about 20 wires, and;
    f. wherein a substantial number of the wires forming the expandable cage are made of radiopaque material.

2. The vascular catheter of claim 1 wherein said expandable cage contains a partially expanded helical coil.

3. The vascular catheter of claim 1 wherein the radiopaque material is a platinum-nickel alloy.

* * * * *